United States Patent [19]

Steiger

[11] 3,948,727

[45] Apr. 6, 1976

[54] BIOLOGICAL INDICATOR AND METHOD OF PRODUCTION THEREOF

[75] Inventor: Eberhard Steiger, Leipzig, Germany

[73] Assignee: VEB Kombinat Medizin-und Labortechnik, Liepzig, Germany

[22] Filed: June 7, 1973

[21] Appl. No.: 367,988

[52] U.S. Cl. .............................. 195/54; 195/103.5 R
[51] Int. Cl.²........................................... C12K 1/04
[58] Field of Search ...... 195/53, 54, 72, 100, 103.5, 195/127, 59, 65; 23/253 TP; 426/61

[56] References Cited
UNITED STATES PATENTS

| | | | |
|---|---|---|---|
| 3,072,538 | 1/1963 | Baptist | 195/100 |
| 3,585,112 | 6/1971 | Ernst | 195/103.5 |

*Primary Examiner*—A. Louis Monacell
*Assistant Examiner*—R. B. Penland
*Attorney, Agent, or Firm*—Nolte and Nolte

[57] ABSTRACT

Biological indicator for the reproducible control of the conducting of chemical sterilizations, comprising a dried suspension of native bacteria originating from a spore soil and now free of their soil biotope.

12 Claims, No Drawings

BIOLOGICAL INDICATOR AND METHOD OF PRODUCTION THEREOF

This invention relates to a biological indicator and especially a biological indicator article alone or in combination with a chemical indicator for reproducible control of the conducting of chemical sterilizations, and to a method of producing the biological indicator article alone or in combination with a chemical indicator.

Biological indicator articles for chemical sterilizations have involved the use of vegetative or spore forming microorganisms in pure cultures or in spore soils. It has been found that the physical and chemical structure of the spore soils is too variable. This is especially so regarding the composition of the organic and inorganic constituents, the water take-up capacity, changes in pH value and particle size distribution. Moreover, the resistance of spore soils is very influenced by chemical agents used for the sterilization so that the effectiveness thereof on a time scale sometimes varies by hours. Also, testing with spore soils is very expensive and the inponderables inherent in such use thereof result in lack of reproducible control in the conducting of chemical sterilizations. Therefore, frequently microbiologically pure cultures are used instead of spore soils.

Microbiologically pure cultures lack, however, the resistance necessary for a biological indicator. Their characteristics fluctuate within wide limits and are dependent on the frequency and type of cultivation and, also, on the age of the culture. A few indicator germs, such as staphylocuccus, coli bacteria and the like when dried on a substrate have only a short storage life. Selection of microbiologically pure cultures as sterilization indicators is strictly limited to apathogenic germs. Moreover, the cultivation of the bacteria cultures and the deposit thereof on a suitable substrate or carrier is quite expensive since special precautions are necessary to exclude undesired germs.

It is an object of the invention to eliminate the disadvantages of the heretofore used indicator articles by providing novel biological indicator articles for controlling the conducting of chemical sterilizations and a method of producing such indicator articles, the indicator articles optionally being combined with a chemical indicator.

The biological indicator articles of the present invention have a number of desirable characteristics. They guarantee reproducible test results, that is, with the exception of normal biological statistical variations, there are no other imponderables present which lead to test results which are not significant and not checkable. They are simple and inexpensive to produce and exhibit a resistance which is stable over a long period of time. In order to avoid confusion between sterilized and non-sterilized indicator articles in serial testing, as for example in industrial sterilizations, they exhibit a suitable indication. Moreover, they exhibit sufficient resistance to the chemical sterilizing agents to provide a safety margin which is adjustable as desired within predetermined limits.

According to the invention, the biological indicator is produced in the form of a germ suspension from native germs without the soil biotope thereof. This indicator is fabricated into a biological indicator article by drying the suspension in a receiving body, preferably in a plastic tube. To increase the resistance of the biological indicator the dried microorganism can be provided with a protective layer, which is preferably constituted of protein. Also for this purpose, and in addition for the inhibition of the entry of gaseous sterilization agent into the interior of the tube, the tube ends are sealed closed.

By including a chemical indicator, an indication is given if the biological indicator has already been exposed to a sterilization process. The chemical indicator, a label and the biological indicator in the form of an indicator article are packed in a germ impermeable casing. It is especially advantageous that the chemical indicator be selected for an ethylene oxide sterilization and particularly that the chemical indicator be bromcresol purple in a conducting salt solution.

An additional measure for changing the resistance is mixing the germ suspension for the biological indicator with a subliminal dosage of the agent which is to be used for the sterilization.

The invention is also directed to the method of producing the biological indicator. According to the method of the invention, in a first step the native germs of the spore soil are separated from their biotope by suspension in a liquid. After repeated agitations at predetermined time intervals and removal of deposited solid constitutents, in a second step the supernatant germ suspension is decanted. Or, after the agitation, the solid constituents are separated from the germ suspension by filtration. To suspend the spore earth and simultaneously vary the resistance of the biological indicator, distilled water, ethyl alcohol, acetone, sodium chloride solution or other suitable medium may be used.

According to another aspect of the invention, the resistance of the biological indicator may be altered by briefly exposing the germ suspension to a temperature above 60°C. or by briefly exposing the spore soil, before the suspension, to the chemical sterilization agent.

In yet another aspect of the invention, less resistant germs can be eliminated from the germ suspension by heating the suspension to a temperature of about 80°C. for about an hour or by mixing the suspension with a subliminal dose of the sterilizing agent to be used.

The germ count per ml. in the germ suspensions of the invention can be determined. In a preferred embodiment of the invention, a germ suspension having a germ count per ml. of $10^6$ to $10^9$, preferably $10^6$, is pipetted into a plastic tube 40 mm. long, 4 mm. in external diameter and having a wall thickness of 0.7 mm. and, thereafter the packaged suspension is dried at a temperature between room temperature and about 40°C.

The invention is further described in the following examples.

EXAMPLE 1

Production of biological indicator:

The spore soil in a conventional manner is suspended in distilled water whereby the native germs are separated from their biotope. After several periodic agitations and settling of the solid constituents, the supernatant germ suspension is decanted. Finally, into a polyvinyl chloride tube 40 mm. in length and having an external diameter of 4 mm. and a wall thickness of 0.7 mm. is pipetted the resultant germ suspension having a germ count of $10^6$ per ml. whereafter the suspension is dried in the pouch at a temperature between room temperature and about 40°C.

Adjustment of the resistance of the biological indicator:

To increase its resistance, the germ suspension is heated briefly to above 60°C. An increase in resistance can also be obtained by briefly exposing the germ soil or the germ suspension to the chemical sterilization agent or by coating the dried microorganisms, preferably with protein.

Elimination of less resistant germs:

The germ containing solution is heated for an hour at 80°C. or is mixed with a subliminal dose of the chemical agent to be used for the sterilization.

EXAMPLE 2

Production of biological indicator:

Distilled water, ethyl alcohol, acetone, sodium chloride solution or other suitable medium is used to suspend the spore soil. The solid constituents are removed from the suspension by filtration. The germ suspension is used to make a biological indicator article as in Example 1.

Adjustment of the resistance of the biological indicator:

Instead of by the methods of Example 1, here the resistance is adjusted by selection of the medium for the dispersion.

EXAMPLE 3

Production of an indicator article including both a biological indicator and a chemical indicator:

The sealed polyvinylchloride tube of dried germs of Example 1 or Example 2 is sealed along with a chemical indicator and preferably a label in a polyethylene foil which is impervious to germs and about 80 to 100 μm. thick.

The chemical indicator:

Where the chemical sterilization agent is to be ethylene oxide, a conducting salt solution of bromcresol purple, which gives a direct or indirect raction with ethylene oxide, is included in the polyethylene package.

The label sealed in the package indicates the sterilization methods for which the indicator is suitable as well as the date after which the packaged bacteria no longer are effective.

What is claimed is:

1. Biological indicator for the reproducible testing of chemical sterilizations, consisting essentially of a dried suspension of native germs originating from a spore soil and now free of their soil biotope and a receiving body in which the germs are contained, the indicator being essentially free of germs not sufficiently resistant to have withstood heating at 80°C. for 1 hour and the receiving body being impervious to the germs and permeable relative to the chemical sterilizing agent.

2. Biological indicator according to claim 1, in which the receiving body is a plastic tube.

3. Biological indicator according to claim 1, in which the germs are coated with a protective protein layer.

4. Biological indicator according to claim 2, in which the plastic tube containing the germs and a label are enclosed in a germ impervious package which is permeable to the chemical sterilizing agent.

5. Biological indicator according to claim 4, in combination with a chemical indicator enclosed in the germ impervious package.

6. Biological indicator according to claim 5, in which the chemical indicator comprises a conducting salt solution of bromcresol purple.

7. Method of preparing a biological indicator for the reproducible testing of chemical sterilizations, comprising suspending spore soil in a liquid, heating the suspension to a temperature of about 80°C. for a period of about 1 hour, agitating the suspension, permitting the solid constituents to separate, decanting the resultant biotope-free germ suspension and drying the germ suspension.

8. Method according to claim 7, further comprising mixing the germ suspension with a subliminal dose of the agent to be used in the chemical sterilization thereby to alter the resistance of the biological indicator.

9. Method according to claim 7, in which the liquid is distilled water, ethyl alcohol, acetone or a sodium chloride solution, the resistance of the biological indicator being related to the liquid selected for the suspending.

10. Method according to claim 7, further comprising briefly exposing the spore soil to the agent to be used in the chemical sterilization thereby to alter the resistance of the biological indicator.

11. Method according to claim 7, in which the germ count in the suspension is in the range of $10^6$ to $10^9$ germs per ml.

12. Method according to claim 7, in which the drying is at a temperature of room temperature to about 40°C. and prior to the drying the suspension is pipetted into a plastic tube 40 mm. in length, 4 mm. in external diameter and 0.7 mm. in wall thickness and which is germ impervious and permeable relative to a chemical sterilizing agent.

* * * * *